(12) United States Patent
Peruzzo

(10) Patent No.: US 8,628,499 B2
(45) Date of Patent: Jan. 14, 2014

(54) INJECTION DEVICE PREVENTING THE RETURN OF THE PISTON WHEN THE SAFETY SYSTEM IS DEPLOYED

(75) Inventor: Grégory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 624 days.

(21) Appl. No.: 12/744,022

(22) PCT Filed: Nov. 21, 2007

(86) PCT No.: PCT/IB2007/004369
§ 371 (c)(1),
(2), (4) Date: Aug. 31, 2010

(87) PCT Pub. No.: WO2009/066130
PCT Pub. Date: May 28, 2009

(65) Prior Publication Data
US 2010/0324492 A1    Dec. 23, 2010

(51) Int. Cl.
*A61M 5/32* (2006.01)
*A61M 5/315* (2006.01)
*A61M 5/00* (2006.01)

(52) U.S. Cl.
USPC ........... 604/198; 604/192; 604/218; 604/197; 604/263

(58) Field of Classification Search
USPC ......... 604/218, 198, 110, 192, 117, 263, 163, 604/197, 221, 232, 171
See application file for complete search history.

(56) References Cited

U.S. PATENT DOCUMENTS

2011/0230832 A1*    9/2011    Neale et al. ................... 604/110

FOREIGN PATENT DOCUMENTS

| FR | 2 861 310 A1 | | 4/2005 |
|----|---|---|---|
| WO | 02/070054 A1 | | 9/2002 |
| WO | WO02/070054 | * | 9/2002 |
| WO | 2005/030301 A1 | | 4/2005 |
| WO | 2006/111862 A1 | | 10/2006 |
| WO | 2008/035226 A2 | | 3/2008 |

* cited by examiner

*Primary Examiner* — Emily Schmidt
*Assistant Examiner* — Bradley G Thomas, Jr.
(74) *Attorney, Agent, or Firm* — Hoffmann & Baron, LLP

(57) ABSTRACT

The present invention relates to an injection device (1) comprising: -a body (3) receiving a product, having a needle (7) and a piston (5) attached to a piston rod (8) movable between a storage position and an end-of-injection position, -a sleeve (6) for protecting the needle (7), movable between an initial position, where the needle (7) is uncovered, and a final position, where the needle (7) is covered, -biasing means (26) for moving said sleeve (6) from its initial position to its final position, -immobilization means (16, 31) for keeping said sleeve (6) in its initial position, characterized in that: -said piston rod (8) comprises a first portion (9) and a second portion (10), said second portion (10) being able to switch between a locked position, in which said second portion (10) is fixed to said first portion (9) and an unlocked position, in which said second portion (10) is movable with respect to said first portion on a predetermined distance along the longitudinal axis of said piston rod (8).

12 Claims, 10 Drawing Sheets

Figure 1:
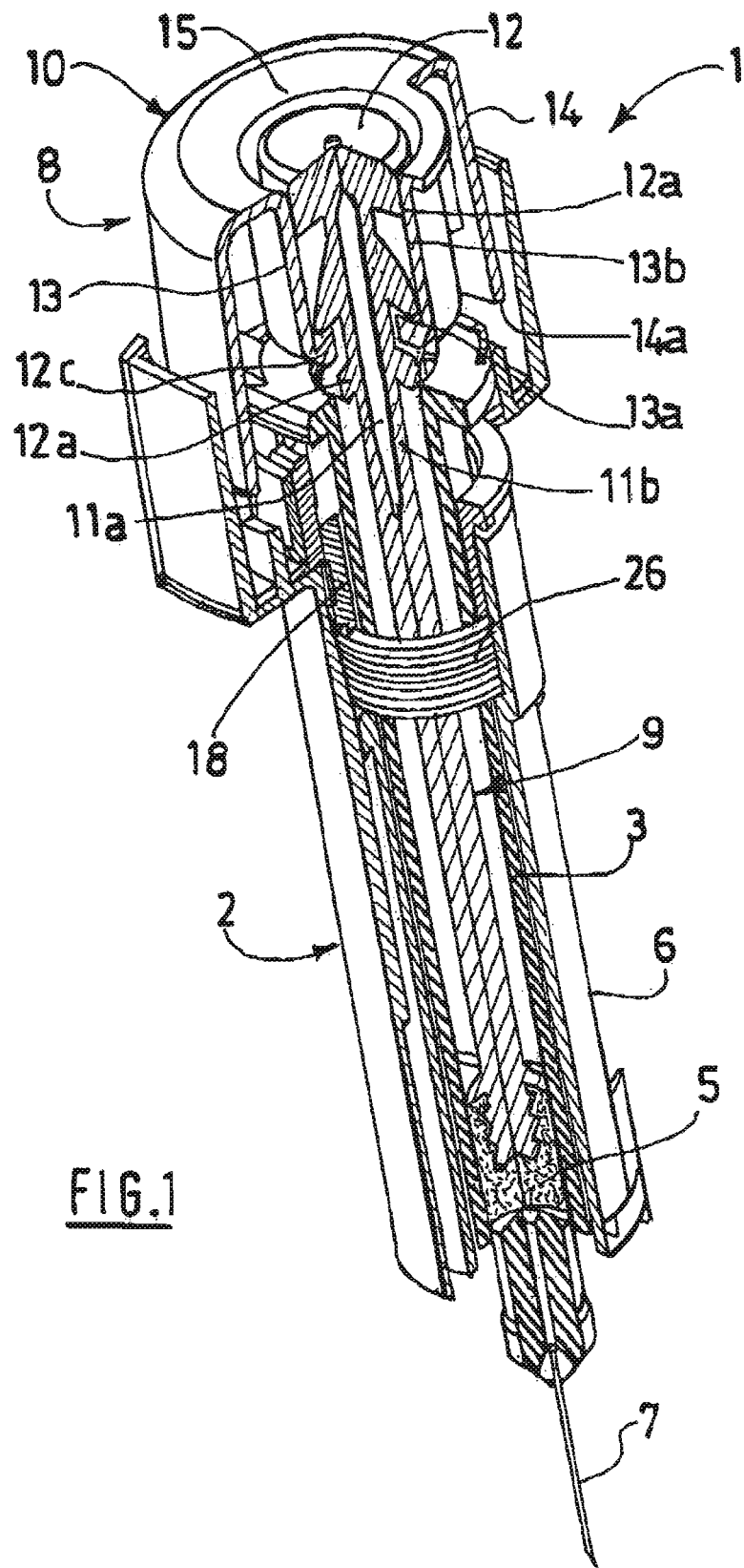

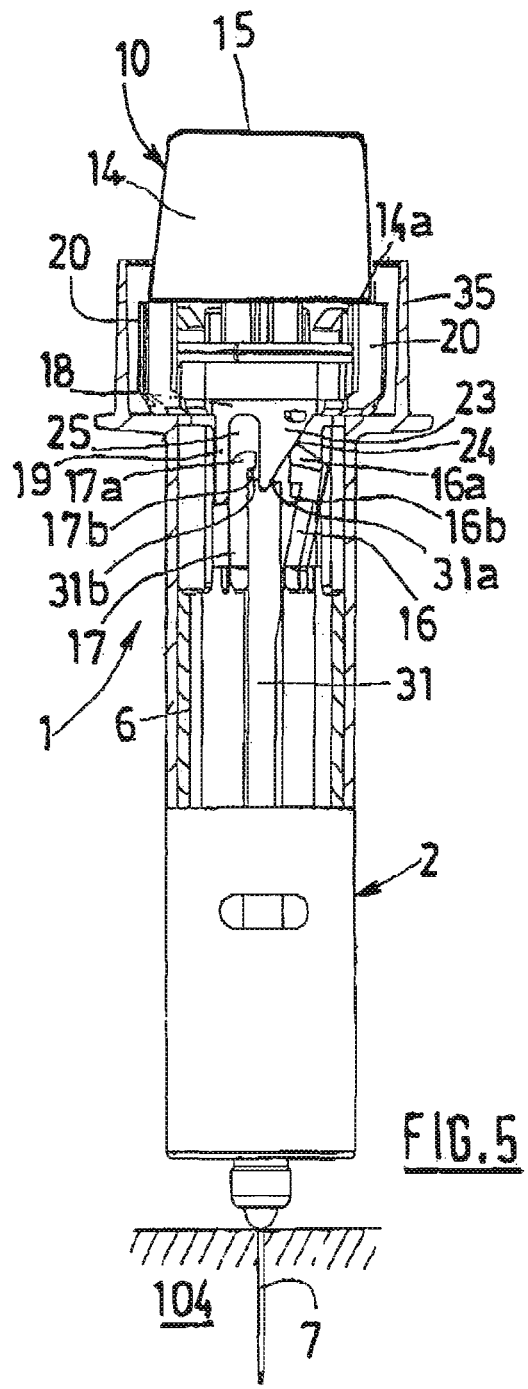
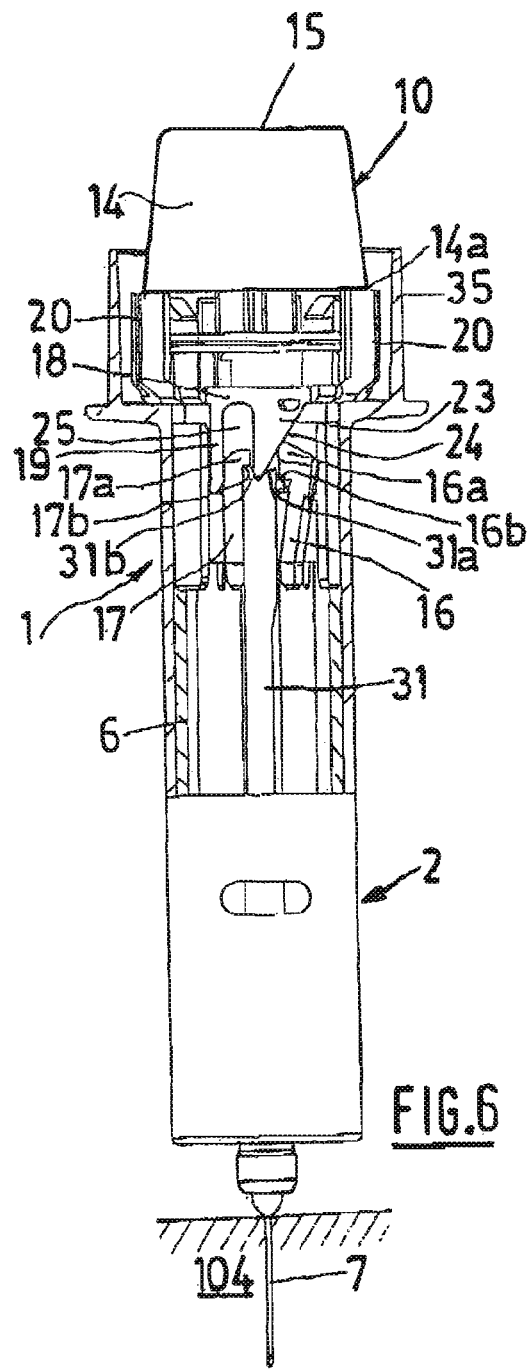

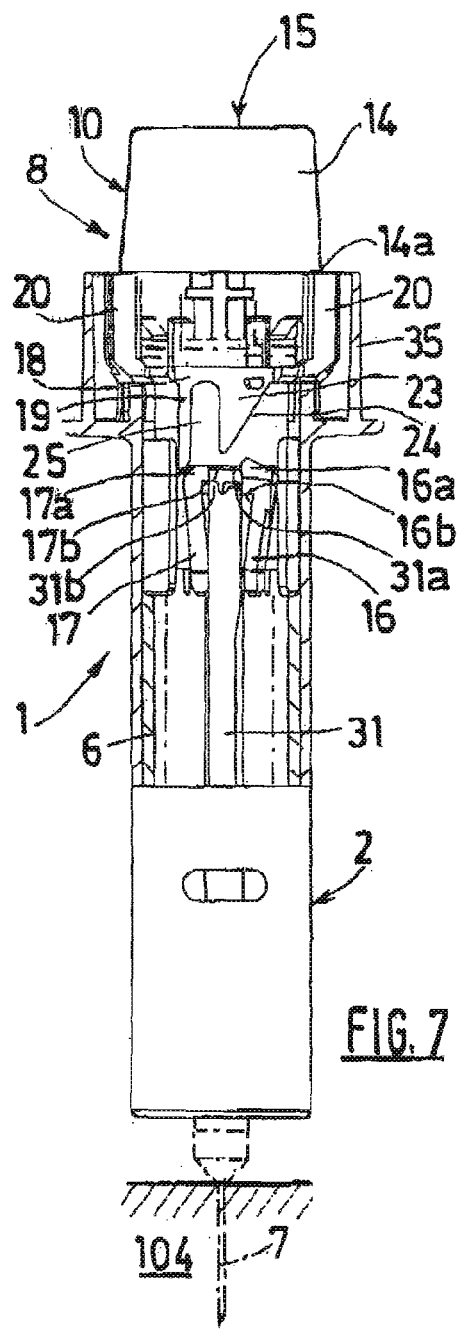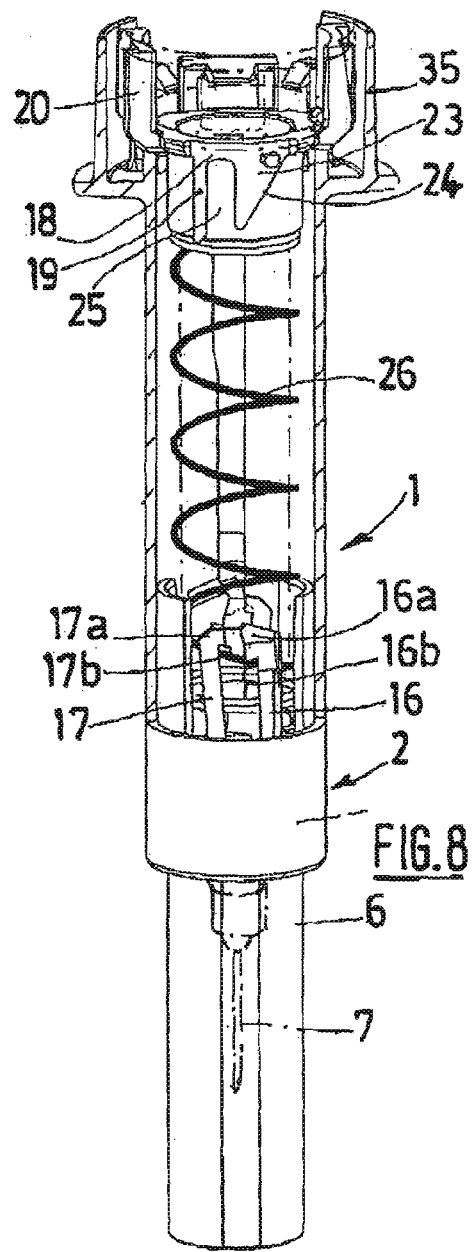

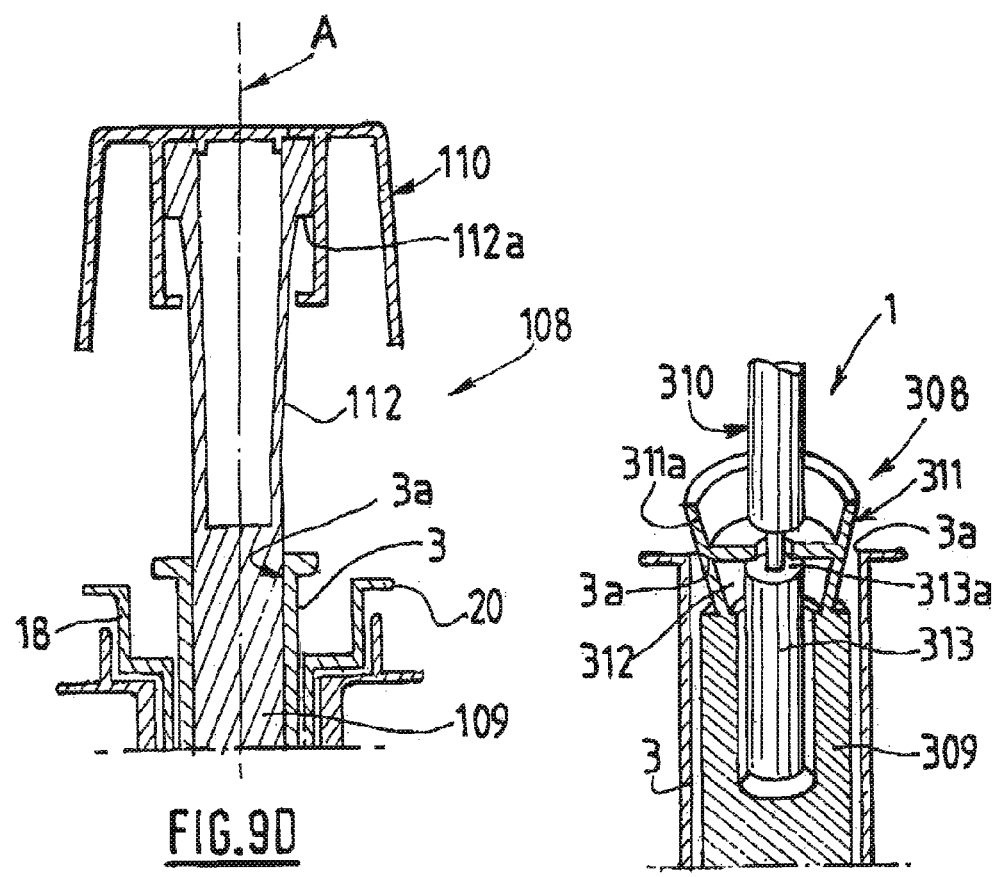
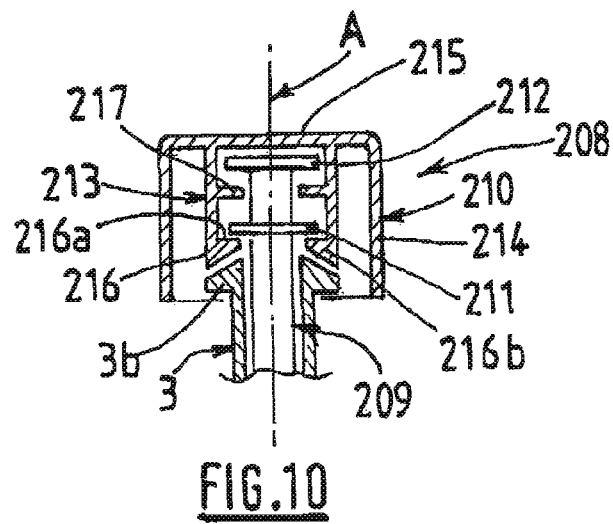

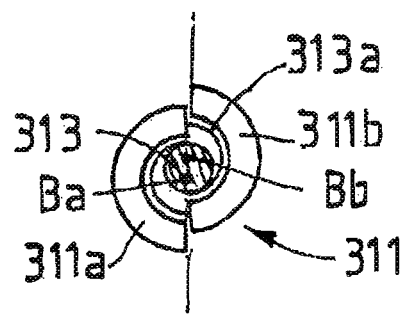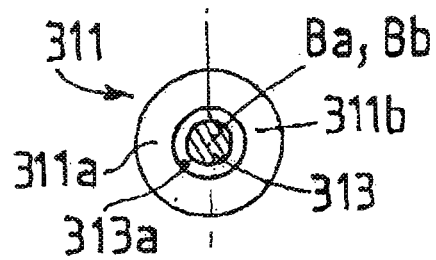
FIG.11A  FIG.11B
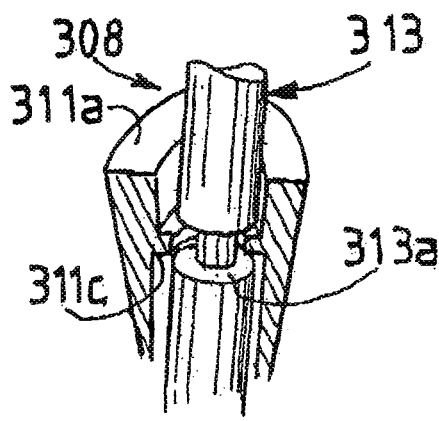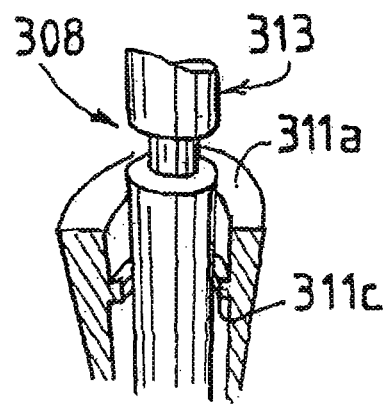
FIG.12A  FIG.12B
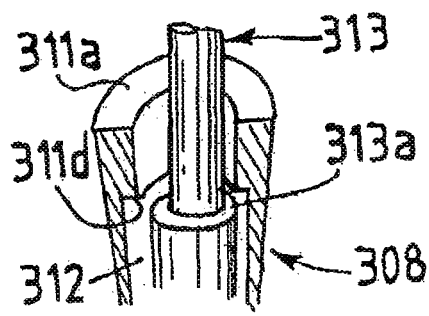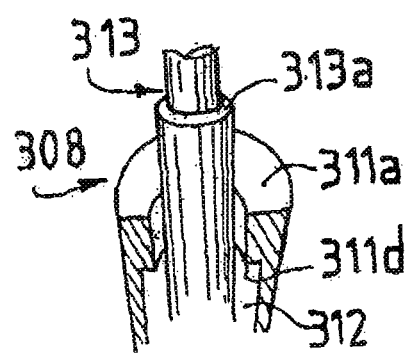
FIG.13A  FIG.13B

INJECTION DEVICE PREVENTING THE RETURN OF THE PISTON WHEN THE SAFETY SYSTEM IS DEPLOYED

The present invention relates to an injection device, particularly for medical use, such as syringes, particularly provided with a safety system aimed at protecting the injection needle after use.

In this application, the distal end of a component or of a device means the end furthest away from the hand of the user and the proximal end means the end closest to the hand of the user. Similarly, in this application, the terms "in the distal direction" and "distally" mean in the direction of the injection, and the terms "in the proximal direction" and "proximally" mean in the direction opposite to the direction of injection.

Injection devices, such as syringes, are well known. These injection devices are usually provided at their distal end with an injection needle that is designed to be inserted into the skin of a patient, and through which the product to be injected passes to the injection site. Normally, these syringes are provided with a piston rod whose distal end comprises a piston which, during the injection phase and under the action of a distal pressure exerted by the user on the piston rod, pushes the product through the injection needle.

One of the constant problems presented by the injection devices is the risk of accidental pricks likely to occur after the injection.

In order to minimize these risks, it is known practice to furnish the syringes with means of protecting the needle after injection: these protection means may for example be in the form of a sleeve sliding relative to the syringe and required to cover the needle after the injection and the withdrawal of the needle from the injection site.

Certain of these protection means must be activated manually, the sleeve having to be moved manually by the end-user to cover the needle. Consequently, these protection means are not very reliable and not very practical to use. To remedy these disadvantages, injection devices have been designed with protection means that are automatically activated, for example by the movement of the piston rod which, when it reaches a predetermined position, releases the sleeve then deployed without additional manual intervention, by elastic means, for example a spring forcing its distal movement at the end of injection.

However, it happens that the automatic protection means are activated while the needle is still in the skin of the patient. In such a case, the sleeve begins to deploy and is then stopped by the skin of the patient against which it is pressed by the spring. The spring can therefore not deploy further in the distal direction and tends to deploy in the proximal direction, which causes the piston rod, and hence the piston, to rise again in the proximal direction into the body of the injection device. In other cases as described hereinafter, the piston rod is caused to rise again by the means for activating the protection means returning elastically to their initial position.

The user may then be confronted with a problem of reabsorption of the injected product due to the return movement of the piston rod, and hence of the piston, in the proximal direction. This return movement is usually limited in distance: however, it is sufficient to cause a portion of the product previously injected into the body of the patient to return into the body of the syringe, thereby causing an incorrect dosage of the injected product. The recommended dose of product is not injected in its totality and serious consequences for the patient may result therefrom.

Thus, there is the need for an injection device comprising automatic means of protecting the needle making it possible to prevent the phenomenon of the return of the piston in the proximal direction after injection, in particular when the injection needle remains at least for a moment in the skin of the patient after the end of the injection and when the automatic protection means are activated before it is withdrawn.

Publication WO 03/068298 A1 describes an injection device provided with automatic protection means activated by the piston rod when the latter arrives at the end of travel towards the end of the dose. The protection means comprise a sleeve held in a sheath by elastically flexible lateral lugs designed to be deflected by the head of the piston rod when the latter arrives at the end of travel. The spring provided for deploying the sleeve is placed between the sheath and the sleeve itself. Thus, if, at the end of injection, while the needle is still in the injection site, the user stops pressing on the piston rod, the spring will only have the effect of pressing the sleeve towards the skin of the patient without causing the piston rod to rise again. Nevertheless, this injection device has the major disadvantage of not allowing the moment when the protection means are activated to be controlled. It is therefore difficult, even impossible, to perform the injection of the end of the dose followed by the activation of the protection means. Either the activation might take place before the end of the dose is injected, and then the sleeve is released and pressed against the skin when the whole dose of product has not yet been injected, or the end of the dose might be injected without activation. Indeed, it is very difficult to reach a control level of the industrial process allowing the required accuracy of the dimensions and tolerances. Furthermore, the sheath of this injection device comprises elastically flexible intermediate lugs placed between the lateral lugs and the head of the piston rod. When the automatic protection means are triggered, if the user relaxes the pressure of the piston rod, the intermediate lugs return to their undeflected position causing the piston to rise again, hence a risk of reabsorption of the previously injected product.

There is therefore also the need for such an injection device making it possible to trigger the activation of the protection means at the moment desired by the user and to ensure that the end of the dose of product is injected without reabsorption.

Specifically, one of the problems encountered with the automatic protection means is the risk of activating them prematurely or inadvertently, during their use, even during the manufacture and/or assembly of the injection devices. Another associated risk is that of, after activation of the protection means, no longer being able to inject the end of the dose. Also, to alleviate these problems, the injection devices must be manufactured with extremely tight production tolerances aimed at the end of the dose coinciding with the activation of the activation means. These production tolerances are difficult to guarantee; the industrial processes for manufacturing the injection devices are thereby complicated and slowed and the injection device is more costly.

Publication WO 2005/030301 A1 describes an injection device provided with automatic protection means activated by the piston rod when the latter arrives at the end of travel towards the end of the dose. The automatic protection means comprise a sleeve designed to be deployed by a spring. Before activation, this sleeve is kept in the withdrawn position by immobilization means. This injection device also comprises means of retaining the sleeve. These retention means make it possible to prevent the deployment of the sleeve after activation of the immobilization means. The retention means are released by simply relaxing the distal pressure applied to the piston rod to allow the deployment of the sleeve. This injection device nevertheless does not make it possible to remove the risk of reabsorption when the user relaxes the pressure on the piston rod before withdrawing the injection needle from the injection site.

There is therefore the need for an injection device that prevents the return of the piston after injection and that is provided with needle protection means that can be activated automatically but only when the end-user so decides, making it possible, after activation of the protection means, to allow the injection of the end of the dose, and that is easy to manufacture.

Moreover, such an injection device must be of simple use for the user. In this view, it must appear as reassuring for the user and must not present any features capable of instilling doubt in the user's mind that the device is not safe or not working.

The object of the invention is therefore to provide an injection device, particularly a syringe, of simple and reassuring use for the user, provided with needle protection means activated automatically at the end of injection, the activation of the needle protection means being controlled by the user, which prevents inadvertently activation of the automatic protection, thus providing perfect safety against the risks of accidental pricks, and which also prevents the return of the piston after injection. Another object of the invention is to propose such an injection device with needle protection means making it possible to inject the end of the dose and capable of being easily manufactured industrially.

The present invention relates to an injection device comprising at least:
  a body designed to receive a product to be injected, said body being provided at its distal end with an injection needle, said body receiving a piston rod and a piston capable of moving in said body between a storage position and an end-of-injection position and of pushing said product through said injection needle,
  protecting means of said injection needle comprising at least:
  a sleeve for covering said injection needle, said sleeve being movable relative to said body between at least an initial position, in which said injection needle is uncovered, and a final position, in which said injection needle is at least partially covered,
  biasing means arranged to aim at moving said sleeve between said initial and final positions,
  immobilization means arranged to aim at holding said sleeve in at least one of said initial and final positions,
  said injection device being characterized in that:
  said piston rod comprises at least a first portion and a second portion, said first portion and said second portion being axially connected to each other and able to switch between at least a locked position, in which said first portion and said second portion are fixed with respect to each other along the longitudinal axis A of said piston rod, and an unlocked position, in which said first portion and said second portion are allowed to move apart from each other at least on a predetermined distance along the longitudinal axis A of said piston rod.

In the present application, by the fact that the first and the second portions of the piston rod are axially connected together, it is meant that the first and second portions remain coupled one to the other along the longitudinal axis of the piston rod, whatever their position, locked or unlocked.

Document U.S. Pat. No. 4,915,692 describes an injection device comprising a piston rod comprising two portions, a rod portion and a portion for connection to the piston. However, the portion for connection is not allowed to move freely in longitudinal translation relative to the rod portion between two predefined positions.

The injection device according to the invention makes it possible to prevent the piston from moving backwards again when the needle protection means are triggered at the end of injection, particularly when this triggering is performed while the needle is still in the injection site.

Specifically, because a portion of the piston rod is able to move separately from the other portion, when said first and second portions are in the unlocked position, for example at least over a predetermined distance, the proximal deployment of the biasing means on the piston rod, when the sleeve is pressing against the injection site, is absorbed by the proximal movement of that portion, this absorption allowing the other portion to be unaffected and remain immobile relative to the body of the injection device. Thus, the injection device according to the invention makes it possible to prevent the reabsorption of part of the medicine already injected, when the sleeve, that is to say the needle protection means, moves into place automatically.

The injection device according to the invention therefore makes it possible to limit the risks due to a faulty, in particular diminished, administration of the dose of prescribed medicine while offering safe use.

Moreover, because the first and second portions are able to adopt a locked position in which they are fixed to each other, in particular before use, the user does not have the feeling that an element is free to move inside the injection device and is therefore reassured. In such a locked position, the first and the second portions are not movable with respect to each other along the longitudinal axis of the piston rod, regardless of any pressure exerted by a user on said first and/or second portions.

In an embodiment of the invention, the injection device comprises
  locking means designed for maintaining said first portion and said second portion in said locked position, a first part of said locking means being located on said first portion of said piston rod and a second part of said locking means being located on said second portion of said piston rod, said first and second parts of said locking means being engaged into each other when said first and second portions are in said locked position, and
  deactivating means designed for releasing said locking means, said deactivating means being capable of cooperating with at least one of said first and second parts of locking means so as to disengage said first part of said locking means from said second part of said locking means and therefore allowing said first portion and said second portion of said piston rod to switch to their unlocked position.

In an embodiment of the device of the invention, the deactivating means are designed to be operated by the displacement of the piston rod at least before said piston rod reaches the end-of-injection position.

In an embodiment of the invention, said first part, respectively said second part, of said locking means comprises at least one flexible element, and said second part, respectively said first part, of said locking means comprises at least one abutment surface, said flexible element being engaged in said abutment surface when said first portion and said second portion of said piston rod are in said locked position, said flexible element being able to move to a deflected position so as to disengage from said abutment surface under the action of said deactivating means.

In an embodiment of the invention, said deactivating means comprise at least part of a proximal end of said body, said part of said proximal end coming in contact with said flexible element at least before the piston rod and the piston reach their end-of-injection position, thereby deflecting said flexible element to its deflected position.

For example, said part of a proximal end of said body may be the inner wall of the proximal region of said body.

In another embodiment of the invention, said part of a proximal end of said body is a flange provided at the proximal end of said body.

In another embodiment of the invention, said first part of said locking means comprises at least a first element having a first longitudinal axis Ba, said second part of said locking means comprises at least a second element having a second longitudinal axis Bb, said first and second longitudinal axis (Ba, Bb) being radially spaced from each other when said first portion and said second portion of said piston rod are in said locked position, at least one of said first and second elements being movable so as to cause said first and second longitudinal axis (Ba, Bb) to become confounded under the action of said deactivating means, thereby causing said first portion and said second portion of said piston rod to switch to said unlocked position.

Said deactivating means may comprise at least the inner wall of the proximal region of the body, said inner wall coming in contact with at least one of said first and second elements and thereby forcing said first and second elements to become axially aligned with each other, at least before said piston rod and said piston reach their end-of-injection position.

In an embodiment of the invention, said biasing means are arranged to aim at moving said second portion in the proximal direction with respect to said first portion when said first portion and said second portion are in said unlocked position.

In an embodiment of the invention, said first portion of said piston rod is provided with a first stop and said second portion of said piston rod is provided with a second stop, said first and second stops being capable of cooperating with each other so as to prevent further proximal movement of said second portion with respect to said first portion, after said second portion has moved proximally with respect to said first portion on said predetermined distance when said first portion and said second portion are in said unlocked position.

In an embodiment of the invention, said predetermined distance is less than 10 mm.

Preferably, said predetermined distance is less than or equal to 5 mm and preferably less than or equal to 3 mm.

In an embodiment of the invention, said biasing means comprise at least a spring.

Another object of the present invention is a piston rod intended to be used with an injection device, characterized in that it comprises at least a first portion and a second portion, said first portion and said second portion being axially connected to each other and being able to switch between at least a locked position, in which said first portion and said second portion are fixed with respect to each other along the longitudinal axis A of said piston rod, and an unlocked position, in which said first portion and said second portion are allowed to move apart from each other at least on a predetermined distance along the longitudinal axis A of said piston rod.

In an embodiment of the invention, the piston rod comprises locking means designed for maintaining said first and second portions in said locked position, a first part of said locking means being located on said first portion of said piston rod and a second part of said locking means being located on said second portion of said piston rod, said first and second parts of said locking means being engaged into each other when said first portion and said second portion are in said locked position, said first and second parts of said locking means being disengageable from each other upon action on said locking means of deactivating means provided on said injection device, allowing therefore said first portion and said second portion to switch to said unlocked position.

Figures 2A, 2B, 2C:
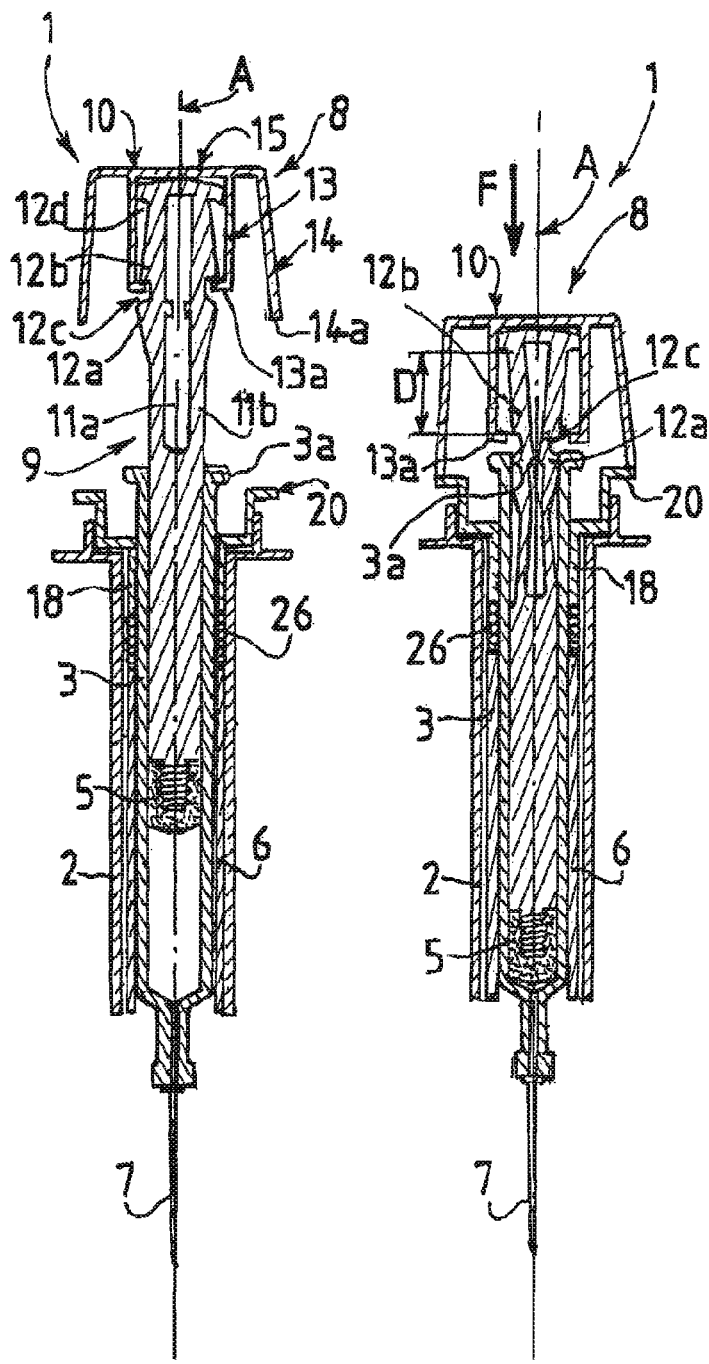
Figure 3:
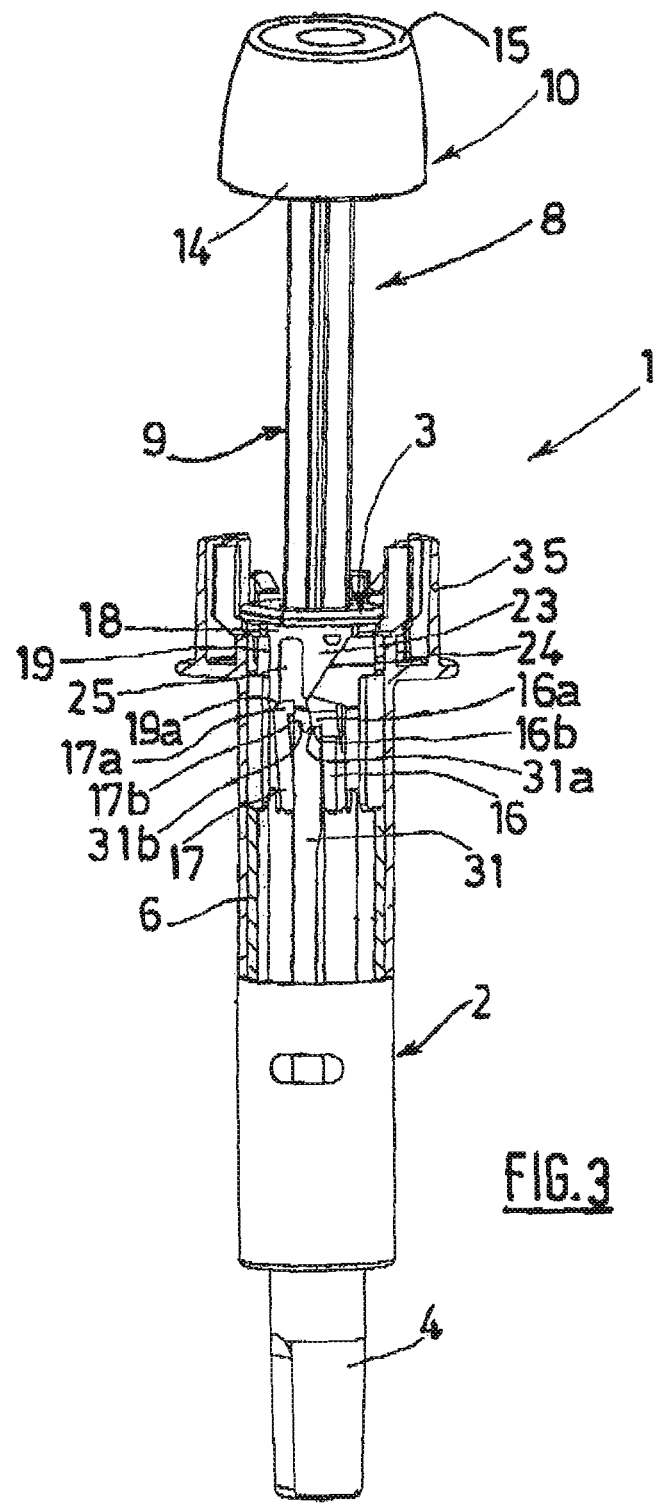
Figure 4:
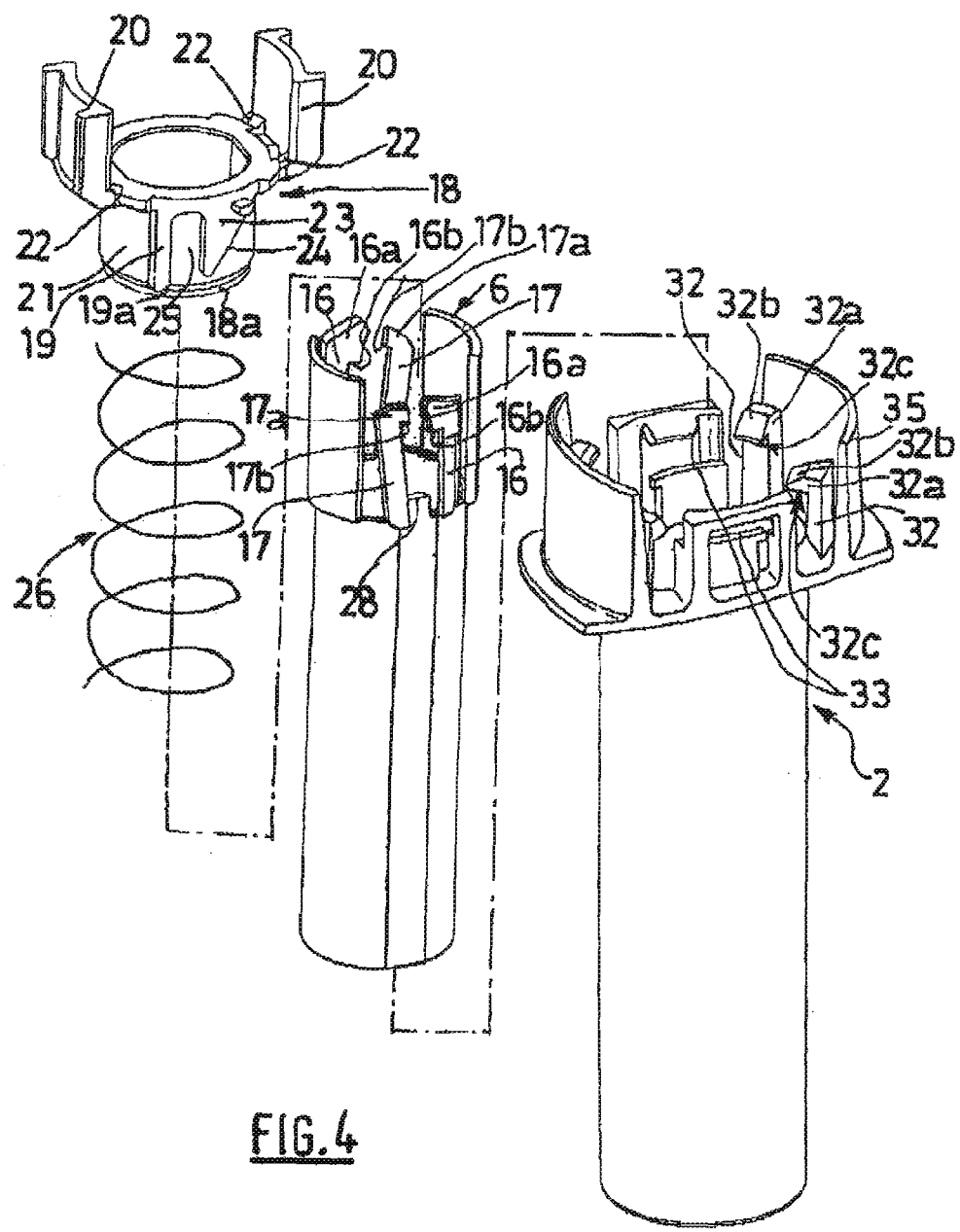
Figures 9A, 9B, 9C:
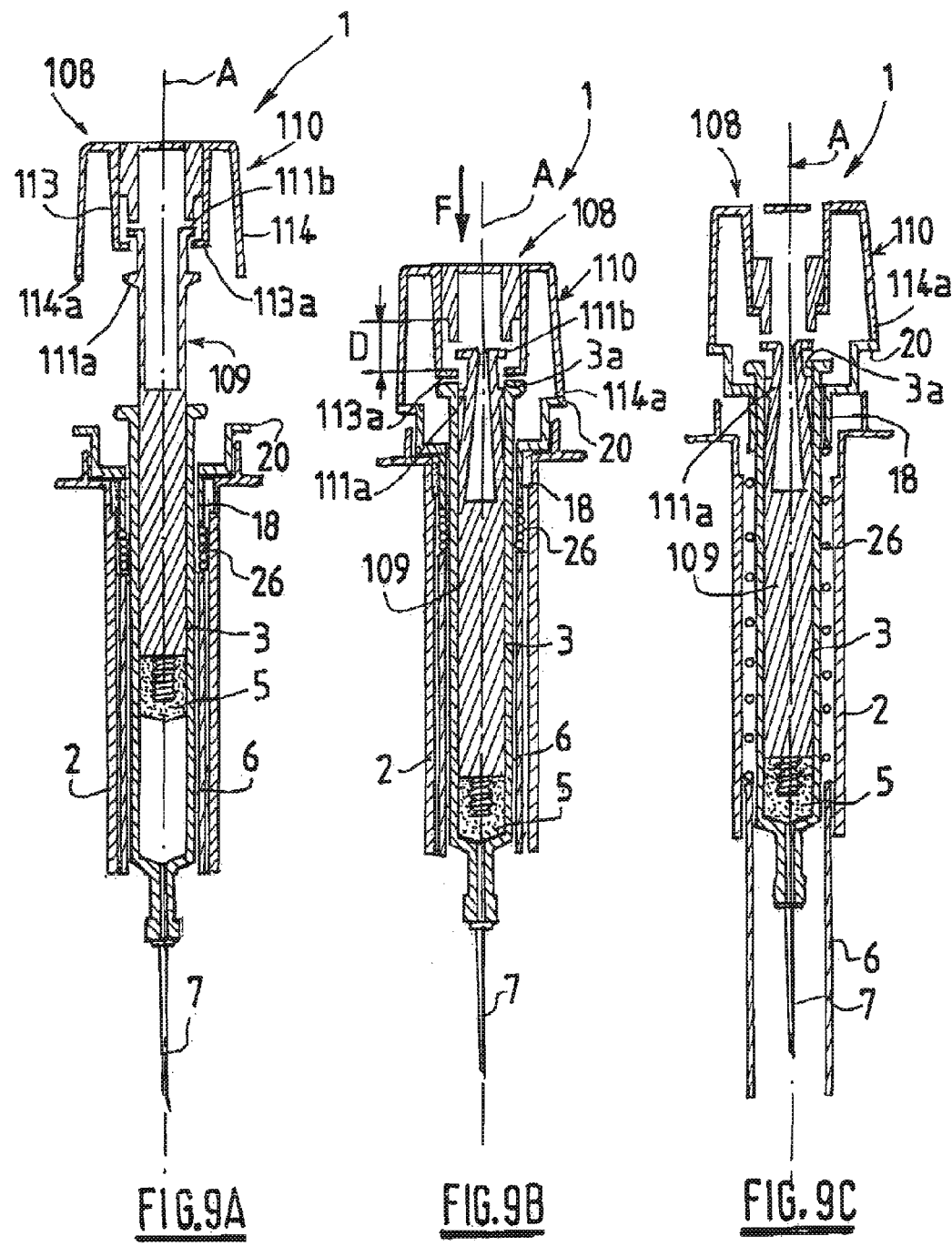
Figure 14B:
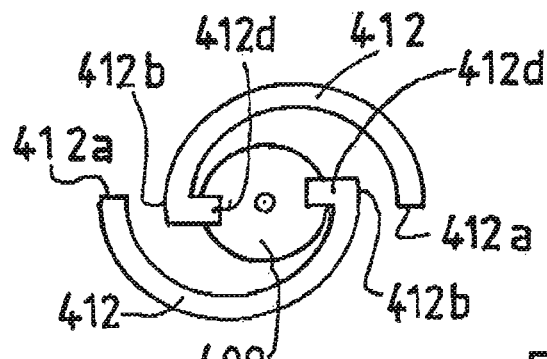
Figure 14A:
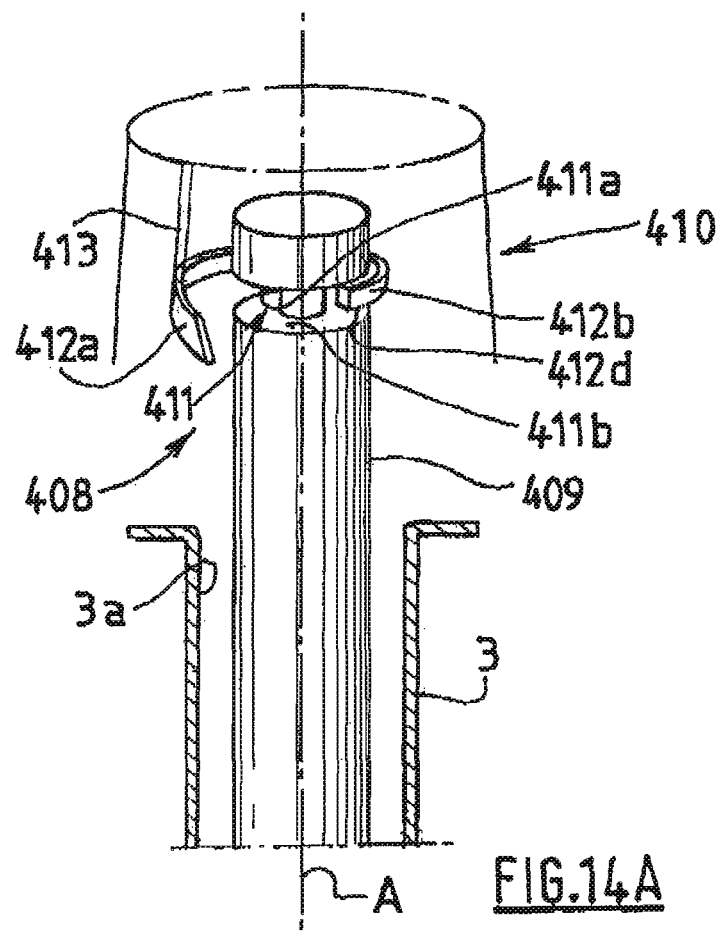

The present invention will now be described in greater detail with the aid of the following description and the appended drawings in which:

FIG. 1 represents a view, in perspective in partial section, of an injection device according to the invention, FIGS. 2A, 2B, and 2C are schematic cross section views of the injection device of FIG. 1, respectively before injection, at the end of injection when the piston rod and the piston reach their end-of-injection position and once the second portion of the piston rod has moved proximally with respect to the first portion of the piston rod after activation of the protection means, FIG. 3 is a side view of the injection device of FIG. 1, in start-of-injection position, FIG. 4 is an exploded view in perspective showing the protection means and the immobilization means of the injection device of FIG. 1, FIG. 5 is a side view of the injection device of FIG. 1, during deactivation of first holding means, FIG. 6 is a side view of the injection device of FIG. 1 showing the holding means deactivated and intermediate holding means activated, FIG. 7 is a side view of the injection device of FIG. 1 during deactivation of intermediate holding means, FIG. 8 is a side view of the injection device of FIG. 1 with the protection means protecting the injection needle, FIGS. 9A, 9B, and 9C are schematic cross section views of another embodiment of a device of the invention, respectively before injection, at the end of injection when the piston rod and the piston reach their end-of-injection position and once the second portion of the piston rod has moved proximally with respect to the first portion of the piston rod after activation of the protection means, FIG. 9D is a partial cross section view of the injection device of FIG. 9A taken after a rotation of 90° along the longitudinal axis of the injection device with respect to FIG. 9A, before injection, FIG. 10 is a partial cross section of another embodiment of a piston rod of an injection device of the invention, FIG. 11 is a partial schematic cross section view of another embodiment of the injection device of the invention, FIGS. 11A and 11B are schematic top views of the locking means of the piston rod of the injection device of FIG. 11, FIGS. 12A, 12B, and 13A, 13B are schematic partial perspective views of two alternative embodiments of the locking means of FIGS. 11A and 11B, respectively in the locked position and in the unlocked position, FIG. 14a is a schematic partial perspective view of another embodiment of a piston rod of the invention in the locked position, FIG. 14B is a partial top view of the piston rod of FIG. 14A.

FIG. 1 shows an injection device 1 according to the invention in the end-of-injection position. This injection device 1 comprises a sheath 2 capable of receiving a tubular body 3 of an injection apparatus, for example of a syringe as represented or of any other receptacle such as a phial, this injection apparatus comprising a product to be injected. The body 3 is provided at its distal end with an injection needle 7. This injection needle 7 may be bonded to the distal end or fitted for example by means of a Luer-type connector. The body 3 houses a piston 5 that is attached to the distal end of a piston rod 8. The piston 5 may be attached to the piston rod 8 by any means, for example screwing, bonding or other means. The piston rod 8 and the piston 5 are capable of moving in the body 3 between a storage position and an end-of-injection position. In particular, under the effect of a distal pressure exerted on the piston rod 8, the piston 5 pushes the product to be injected towards the distal end of the body 3 and therefore through the injection needle 7.

The injection device 1 of the invention of FIG. 1 also comprises protection means of the injection needle 7 provided with a sleeve 6 in the example shown. This sleeve 6 is capable of moving relative to the body 3 so as to be able to adopt at least an initial position, for example a withdrawn position, as shown in FIG. 1, in which the injection needle 7 is uncovered, or else a final position, for example an extended position, as shown in FIG. 8, in which the sleeve 6 entirely covers the injection needle 7, thus preventing the risks of accidental pricking after use. As will be seen hereinafter, the travel of the sleeve 6 from its withdrawn position to its extended position is, in this example, allowed by the user relaxing the distal pressure exerted on the piston rod 8.

In particular, the movement of the sleeve 6 from its withdrawn position to its extended position is due to the return to a relaxed state of previously compressed biasing means, for example elastic means. These elastic means are, in the example shown, in the form of a spring 26.

As appears more clearly in FIGS. 1 to 2C, the piston rod 8 comprises a first portion 9 in the form of a rod to the distal end of which is attached a piston 5, and a second portion 10 placed at the proximal end of the piston rod 8 and forming a head thereto. As explained hereinafter, said first portion 9 and said second portion 10 are axially connected and are able to switch between at least a locked position, in which said second portion 10 is fixed with respect to said first portion 9 along the longitudinal axis A of said piston rod 8, and an unlocked position, in which said second portion 10 is allowed to move at least in the proximal direction with respect to said first portion 9 at least on a predetermined distance along the longitudinal axis A of said piston rod 8.

The locked position of the first and second portions (9, 10) is shown on FIG. 2A: as can be seen on this figure, the first portion 9 is provided in its proximal region with a central bore 11a defining a cylindrical wall 11b for the piston rod 8. Because of the central bore 11a, the wall 11b is radially flexible in direction of the longitudinal axis A of the piston rod 8, as will be seen on FIGS. 2B and 2C. The wall 11b is provided with two outer axially spaced bulges, a first bulge 12a and a second bulge 12b, proximally spaced from said first bulge 12a. The first and second bulges (12a, 12b) define between them a recess 12c. The wall 11b is also provided with a proximal outer stop 12d.

The second portion 10 of the piston rod 8 comprises two concentric cylindrical skirts, an inner skirt 13, and an outer skirt 14, connected together by a transverse wall 15 forming a pressing surface allowing the user to exert a distal pressure on the piston rod 8. The distal end of the inner skirt 13 is provided with an abutment surface 13a.

Before injection, in the locked position of the second portion 10 as shown on FIG. 2A, the abutment surface 13a is engaged in the recess 12c. The second portion 10 is therefore fixed with respect to the first portion 9: the second portion 10 can not move with respect to the first portion 9 along the longitudinal axis of said piston rod 8, neither in the proximal direction nor in the distal direction, regardless of any pressure exerted or not by a user on said first or second portions. The flexible wall 11b, the outer bulges 12a and 12b, the recess 12c and the abutment surface 13a therefore form locking means for maintaining the first and second portions (9, 10) in their locked position. Of course, because of the industrial process constraints, it may happen that, in the locked position of the first and second portions, said second portion 10 may move with respect to the first portion 9 on a slight distance; for instance, it could be considered that a slight movement of the second portion 10 with respect to the first portion 9 of less than or equal to 1 mm, preferably less than or equal to 0.5 mm, more preferably less than or equal to 0.1 mm length along the longitudinal axis of said piston rod 8 would still refer to a locked position of the first and second portions (9, 10), such a distance being short enough not to induce product characteristics which would look like or sound like quality defaults of the product.

FIG. 2B shows the deactivation of these locking means by deactivating means, under distal force F applied by a user on the pressing surface 15 of the piston rod 8: in the embodiment shown on FIGS. 2A to 2C, the deactivating means are under the form of the inner wall 3a of the proximal region of the tubular body 3. As will be explained hereinbelow, during the injection, the piston rod 8 moves distally: at the end of injection, at least just before the piston 5 reaches its end-of-injection position, the first bulge 12a of the flexible wall 11a comes in contact with the inner wall 3a of the proximal region of the tubular body 3 as shown on FIG. 3A. The inner wall 3a of the proximal region of the tubular body 3 presses radially and inwardly the first bulge 12a which causes the wall 11b to be deflected inwardly and radially as shown on FIG. 2B. The second bulge 12b is consequently radially and inwardly deflected, thereby freeing the abutment surface 13a. The first and second portions (9, 10) of the piston rod 8 are therefore in their unlocked position.

FIG. 2C shows the first and second portions (9, 10) in their unlocked position once the second portion 10 has moved proximally with respect to the first portion 9, after the movement of the sleeve 6 toward its extended position. As will be explained hereinafter, at the moment the sleeve 6 is deployed over the injection needle, the second portion 10 is caused to move proximally with respect to the first portion 9. As appears on FIG. 2C, once it has moved proximally on a predetermined distance D, the second portion 10 is prevented from further proximal movement by the abutment surface 13a of the second portion 10 coming in contact with the proximal stop 12d of the first portion 9.

The operation of an embodiment of an injection device 1 of the invention will now be described in reference to FIGS. 1 to 8.

In FIG. 3, the injection device 1 according to the invention is shown in initial position before injection and the injection needle 7 is still covered by a cap 4.

As shown in FIGS. 3 and 4 and as will appear more clearly in FIGS. 5 and 6, the injection device 1 comprises first holding means for immobilizing the sleeve 6 in its withdrawn position during at least the beginning of a phase, called the injection phase, and this is so irrespective of whether the pressure exerted on the piston rod 8 is increased or relaxed. These first holding means comprise two longitudinal protrusions 31 made on the inner surface of the wall of the sheath 2 and two elastically flexible immobilization lugs 16 extending axially in the proximal direction from the proximal end of the sleeve 6. Preferably, the protrusions 31 are diametrically opposed. Each protrusion 31 comprises, at its proximal end, an immobilization surface 31a provided in relief and each immobilization lug 16 is provided at its proximal end with an immobilization hook 16a whose distal face 16b is capable of resting on the immobilization surface 31a of the protrusion 31 placed opposite. As will be explained hereinafter, these first holding means for immobilizing the sleeve 6 are capable of being released automatically during the injection, said sleeve 6 being then kept in an intermediate position, in which the injection needle 7 is uncovered, by intermediate holding means described hereinafter.

As shown in FIGS. 3 and 4 and as will appear more clearly in FIGS. 5 and 6, the injection device 1 of FIGS. 1-8 also comprises intermediate holding means for retaining the sleeve 6 in an intermediate position during at least the end of the injection phase, after automatic release of the first holding means. These intermediate holding means comprise the two longitudinal protrusions 31 previously described. Accordingly, each longitudinal protrusion 31 comprises at its proximal end a retention surface 31b provided in relief. The intermediate holding means also comprise two elastically flexible retention lugs 17, extending axially in the proximal direction from the proximal end of the sleeve 6. Each retention lug 17 is provided at its proximal end with a retention hook 17a whose distal face 17b is capable of pressing on the retention surface 31b of the protrusion 31 placed opposite.

As will be explained hereinafter, in the example described on FIGS. 1-8:

before and at the start of injection (see FIG. 3), the intermediate holding means for retaining the sleeve 6 are in an inactive position in which the retention lug 17 is at rest, flexed laterally, the retention hook 17a therefore not being in the alignment of the protrusion 31: the distal face 17b of the hook 17a is therefore not engaged with the retention surface 31b of the protrusion 31 and does not retain the distal translation of the sleeve 6, this translation then still being prevented by the first holding means, during injection (see FIG. 5), more precisely towards the end of the injection, the intermediate holding means move to a preactivation position: more precisely, the retention lug 17 is straightened under stress so that the retention hook 17a comes in the alignment of the protrusion 31 without however pressing on this protrusion, then (see FIG. 6), the first holding means are released, the sleeve 6 moves distally over a short distance until the distal face 17b of the retention hook 17a comes to press on the retention surface 31b of the protrusion 31: the intermediate holding means are then in an active position and prevent the distal translation of the sleeve 6, the sleeve being then in an intermediate position, at the end of injection (see FIG. 7), the intermediate holding means are deactivated by relaxing the pressure applied on the second portion 10 which, acted upon by the spring 26, moves proximally, releasing, via an intermediate element described hereinafter, the retention lug 17 which flexes to its rest state, then disengaging the retention hook 17a from the protrusion 31 and allowing at the end of injection the movement of the sleeve 6 from its intermediate position to its extended position.

As appears in FIGS. 3 and 4, the injection device 1 also comprises an intermediate element, namely a ring 18 situated in the extreme proximal portion 35 of the sheath 2. The extreme proximal portion 35 of the sheath 2 comprises coupling lugs 32, each coupling lug 32 comprising a radial crank 32a whose distal face 32c is designed to retain the proximal face of the ring 18 in the proximal direction, said radial crank 32a comprising an internal ramp 32b whose function will be explained hereinafter. The ring 18 is capable of moving relative to the sheath 2, inside the extreme proximal portion 35 of this sheath 2, between the distal faces 32c of the coupling lugs 32 and of the rims 33. The ring 18 comprises means of interaction with the second portion 10 of the piston rod 8 of the injection device 1. In the example shown, these interaction means are presented in the form of two diametrically opposed legs 20 extending in the proximal direction, slightly offset in the radial direction relative to the body 21 of the ring 18 and connected at the proximal end of the ring 18 by radial bridges 22.

As will appear more clearly in FIGS. 5 to 8, the ring 18 also comprises means of activating the intermediate holding means in the form, in the example shown, of the guide lugs 19 extending distally and placed substantially symmetrically on the ring 18. Each guide lug 19 defines a longitudinal recess 25 designed to receive a retention lug 17 in active position. Each guide lug 19 is provided at its distal end with an activation ramp 19a designed to facilitate the flexing and the insertion of the retention lug 17 into the longitudinal recess 25 when the intermediate holding means travel from their inactive to active position. The ring 18 also comprises means of releasing the first holding means, in the form, in the example shown, of a surface 23 protruding radially from the body 21 of the ring 18, this surface 23 being capable of interacting with the immobilization lugs 16 in order to flex them circumferentially. In the example shown, this surface 23 has an external ramp 24 opposite each immobilization lug 16.

The proximal end of the spring 26 presses on the distal end 18a of the ring 18 (see FIG. 4) and its distal end presses on an annular rim 28 made on the inner surface of the sleeve 6 at its proximal end.

In practice, the injection device 1 of FIGS. 1-8 is in the initial position before injection as shown in FIG. 3. In this position:

the first and second portions (9, 10) of the piston rod 8 are in their locked position and the second portion 10 is therefore fixed with respect to the first portion 9, as shown on FIG. 2A, the immobilization lugs 16 are engaged with the immobilization surfaces 31a provided in relief, the spring 26 is in an at least partially compressed state.

The system is thus perfectly locked, with no risk of triggering the activation of the sleeve 6.

To proceed with the injection, the user takes hold of the injection device 1 as shown in FIG. 3, removes the cap 4, applies the injection device 1 to the injection site 104 (see FIG. 5), inserts the injection needle 7 in the injection site 104 and exerts a distal pressure on the piston rod 8, in particular on the pressing surface 15 of the second portion 10 of the piston rod 8.

During this injection phase, under the effect of the distal pressure exerted by the user on the pressing surface 15, because the second portion 10 is fixed to the first portion 9, the whole piston rod 8, namely the first portion 9 and the second portion 10, moves in the distal direction and the first portion 9 pushes the piston 5 towards the distal end of the body 3, thus injecting the product.

As is clear from FIG. 3, during the beginning of this injection phase, the first holding means for immobilizing the sleeve 6 in its initial or withdrawn position remain locked. Thus, the sleeve 6 is kept in its withdrawn position by the first holding means irrespective of the value of the distal force exerted by the user on the piston rod 8. In particular, thanks to the first holding means, the sleeve 6 remains in the withdrawn position, even if the user relaxes the distal pressure that he exerts on the piston rod 8 via the pressing surface 15.

Towards the end of the injection, while the injection needle 7 is still inserted into the injection site 104, as shown in FIG. 5, the second portion 10 of the piston rod 8 of the injection device 1 comes into contact with the ring 18. In particular, the distal end 14a of the outer skirt 14 of the second portion 10 of the piston rod 8 comes into contact with the interaction means, that is to say the legs 20, in the example shown, of the ring 18. By continuing to exert a distal pressure and pushing on the second portion 10 of the piston rod 8, the distal end 14*a* of the outer skirt 14 of the second portion 10 of the piston rod 8 pushes the legs 20 of the ring 18 and the ring 18 is thus moved in the distal direction. Under the effect of this distal movement of the ring 18, the activation ramps 19*a* of the guide lugs 19 of the sleeve 6 straighten the retention lugs 17 and force them into the longitudinal recesses 25 so that the hooks 17*a* are in the trajectory of the protrusions 31 and the intermediate holding means can immobilize the distal translation of the sleeve 6. Successively, the external ramps 24 of the radial protrusion 23 of the intermediate ring 18 deflect the immobilization lugs 16 circumferentially so that they are no longer engaged with the protrusions 31.

Thus, the first holding means for immobilizing the sleeve 6 in its withdrawn position are released and, under the pressure of the spring 26, which tries to return to its relaxed state, the sleeve 6 is moved in the distal direction, over a very short distance, until the distal faces 17*a* of the retention lugs 17 make contact with the retention surfaces 31*b* of the protrusions 31 as shown in FIG. 6. The sleeve 6 is then kept in its intermediate position, which is still a withdrawn position of the sleeve in which the injection needle 7 is uncovered, by the intermediate holding means, so long as the user exerts his pressure on the piston rod 8. In this position, the piston (not visible in FIGS. 5 and 6) is almost at the end of travel in the body 3.

In an embodiment of the invention, the course of the ring 18 is as short as possible in order to avoid the risk for the user to inadvertently stop the distal pressure on the pusher 15 during the releasing of the first holding means for immobilizing the sleeve 6 in its withdrawn position. In embodiments, the course of the ring 18 is less than 10 mm, preferably less than or equal to 5 mm, more preferably less than or equal to 3 mm.

To terminate the injection, the user prolongs the distal movement of the piston rod 8 until the piston 5 reaches the bottom of the body 3 and its end-of-injection position. The injection of the end of the dose is thus assured.

In this end-of-injection position of the piston 5, the inner wall 3*a* of the proximal region of the tubular body 3 has come in contact with the first bulge 12*a* of the flexible wall 11*b* of the first portion 9 of the piston rod 8 as shown on FIG. 2B. The inner wall 3*a* has pressed on said first bulge 12*a* which by consequence has deflected in the radial and inward direction causing the second bulge 12*b* to also deflect in the radial and inward direction, as shown on FIG. 3A. The abutment surface 13*a* of the second portion 10 has therefore disengaged from the recess 12*c* and has been freed. The second portion 10 of the piston rod 8 is therefore in its unlocked position, as shown on FIG. 2B.

In normal use, once the end of the dose has been assured, the user keeps the pressure on the piston rod 8 and withdraws the injection needle 7 from the injection site 104. It is nevertheless possible that, through lack of training, information or attention, the user relaxes the pressure on the piston rod 8 before withdrawing the injection needle 7 from the injection site 104. With other injection devices comprising automatic protection means activated by the movement of the piston rod, this incorrect use would have the effect of causing a reabsorption of the previously injected product, hence an incorrect dose. Specifically, the injection devices of the prior art usually comprise a spring placed between the sleeve and the piston rod which, after activation of the protection means, if the injection needle is still in the injection site and the sleeve is immobilized by the skin of the patient, causes the piston rod to return and hence a reabsorption phenomenon.

The invention makes it possible to remove this problem. Specifically, if, while the injection needle 7 is still inserted in the injection site 104, and the protection means, namely the sleeve 6 in the example shown, have been activated, the user relaxes the pressure that he was exerting on the piston rod 8, the ring 18 is moved in the proximal direction under the effect of the pressure of the spring 26. Accordingly, the surface 23 protruding radially from the body 21 of the ring 18 releases the retention lugs 17 from the longitudinal recesses 25 as shown in FIG. 7. These retention lugs 17 resume their initial, slightly inclined position relative to the longitudinal axis of the injection device 1 and the distal retention faces 17*b* of the hooks 17*a* are no longer engaged with the retention surfaces 31*b* of the protrusions 31. Because the second portion 10 is now in its unlocked position, the proximal movement of the ring 18 at the same time causes, via the legs 20 that push the distal end 14*a* of the outer skirt 14 of the second portion 10 of the piston rod 8 in the proximal direction, the proximal movement of this said second portion 10, as shown on FIG. 2C.

Furthermore, since the injection needle 7 is kept in the injection site 104, the sleeve 6 cannot move in the distal direction because it is immediately stopped by the surface of the skin of the patient.

However, due to the ability of the second portion 10 of the piston rod 8 to move in the proximal direction with respect to said first portion 9 separately from said first portion 9, the first portion 9 of the piston rod 8 remains immobile, at least until further proximal movement of said second portion 10 is prevented by the abutment surface 13*a* of the second portion 10 coming in contact with the proximal stop 12*d* of the first portion 9.

The first portion 9 and the second portion 10 of the piston rod 8 remain axially connected, which eases the assembly and the use of the piston rod and which avoids the use of additional parts.

Thus, the ring 18 continues to move in the proximal direction under the action of the spring 26, and pushes said second portion 10 of the piston rod 8. Thanks to the cooperation of the abutment surface 13*a* and of the proximal stop 12*d*, the second portion 10 is stopped once it has traveled the distance D as shown on FIG. 2C.

During this step, the first portion 9 of the piston rod 8 has not moved. Specifically, because of the particular design of this piston rod 8, the energy of deployment of the spring 26 which, with other injection devices would have caused the reabsorption of the injected product, is here totally absorbed by the proximal movement of the second portion 10 of the piston rod 8 independently from the first portion 9, along the distance D. Consequently, the first portion 9 of the piston rod 8 has remained immobile and the piston 5, which is connected thereto, has not moved either. In particular, it has not been subjected to a return movement. The risk of reabsorption of medicine has thus been prevented.

Preferably, the distance D, that is to say the distance the second portion can travel along with respect to the first portion when the first and second portions are in said unlocked position, is sufficient to absorb the beginning of deployment of the spring 26, measurable as the course of the ring. For example, this distance, symbolized by the letter D in FIG. 2C, may be from 1 to 10 mm. Preferably, this distance D is less than or equal to 5 mm, still preferably less than or equal to 3 mm.

The user may then choose to withdraw the injection needle 7 from the patient at that moment only.

Under the effect of the pressure of the spring 26, the sleeve 6 is then moved in the distal direction and comes to cover the injection needle 7 that is shown in dot-and-dash lines in FIG.

8. Then final holding means (not shown), such as legs, provided on the sheath 2 or on the sleeve 6, capable of engaging recesses provided on the sleeve 6, respectively on the sheath 2, immobilize the sleeve 6 in this final position.

On FIGS. 9A to 9C is shown another embodiment of a piston rod for an injection device of the invention. The references designating the same elements as in FIGS. 1-8 have been maintained.

On FIGS. 9A and 9D is shown a piston rod 108 comprising a first portion 109 and a second portion 110. The first portion 109 comprises two flexible tabs 111 cut in its wall 112. Each flexible tab 111 is provided with two axially spaced outer projections, a first outer projection 111a and a second outer projection 111b, proximally spaced from the first outer projection. The wall 112 is provided with a proximal stop 112a.

The second portion 110 comprises two concentric cylindrical skirts, an inner skirt 113 and an outer skirt 114, connected together by a transverse wall 115 forming a pressing surface allowing the user to exert a distal pressure on the piston rod 108. The distal end of the inner skirt 113 is provided with an abutment surface 113a.

The first and second portions (109, 110) are shown in their locked position on FIGS. 9A and 9D. In this position, the abutment surface 113a is engaged on the distal face of the second outer projection 111b, as shown on FIG. 9A, and the second portion 110 is therefore fixed with respect to the first portion 109.

At the end of injection, at least before the piston rod and the piston reach their end-of-injection position as explained before, under distal force F exerted by a user on the piston rod 108, the inner wall 3a of the proximal region of the tubular body 3 comes in contact with the first outer projections 111a and presses in the radial and inward directions on these first outer projections 111a, as shown on FIG. 9B. This causes the flexible tabs 111 to deflect in the radial and inward directions. As a consequence, the second outer projections 111b are caused to deflect in the radial and inward directions and the abutment surface 113a disengages from the distal faces of said second outer projections 111b, as shown on FIG. 9B.

The first and second portions (109, 110) are therefore in their unlocked position, as shown on FIG. 9B, and the second portion 110 is free to move independently and separately from the first portion 109 along the longitudinal axis of the piston rod 108, at least on a certain distance and in the proximal direction with respect to said first portion 109, said first and second portions (109, 110) remaining axially connected to each other in their unlocked position. At the time of deployment of the sleeve 6 (not shown), as explained before for the embodiment of FIGS. 1-8, in case the user relaxes the pressure on the piston rod 8 before withdrawing the injection needle 7 from the injection site 104, the second portion 110 is caused to move proximally with respect to first portion 109, on a predetermined distance D, as shown on FIG. 9B. As shown on FIG. 9C, the proximal movement of the second portion 110 is caused by the force of the spring 26 pushing the ring 18 in the proximal direction on a short distance, at the time said spring 26 extends in the distal direction in order to deploy the sleeve 6. During the proximal movement of ring 18, the legs 20 enter in contact with the distal end 114a of the outer skirt 114 and the second portion 110 is caused to move in the proximal direction with respect to the first action along the longitudinal axis A of the piston rod 108.

During the proximal movement of the second portion 110, the first portion 9 of the piston rod 8 has remained immobile and the piston 5, which is connected thereto, has not moved either. In particular, it has not been subjected to a return movement. The risk of reabsorption of medicine has thus been prevented.

On FIG. 10 is shown partially another embodiment of a piston rod for an injection device according to the invention. On FIG. 10 is shown a piston rod 208 comprising a first portion 209 and a second portion 210.

The first portion 209 is provided with two axially spaced radial stops, a first outer radial stop 211 and a second outer radial stop 212, said second outer radial stop 212 being distally spaced from said first outer radial stop 211.

The second portion 210 comprises two concentric cylindrical skirts, an inner skirt 213 and an outer skirt 214, connected together by a transverse wall 215 forming a pressing surface allowing the user to exert a distal pressure on the piston rod 208. The distal end of the inner skirt 213 is provided with an inner projection 216 having a proximal abutment surface 216a and a distal sloped surface 216b. The inner skirt 213 is flexible and capable of being deflected in the radial and outward direction.

An inner rim 217, proximally spaced with respect to the inner projection 216 is further provided on the inner skirt 213.

The first and second portions (209, 210) are shown in their locked position on FIG. 10. In this position, the abutment surface 216a is engaged on the distal face of the first outer radial stop 211, as shown on FIG. 10, and the second portion 210 is therefore fixed with respect to the first portion 209.

At the end of injection, at least before the piston rod and the piston reach their end-of-injection position, the distal sloped surface 216b of the inner projection 216 of the second portion 210 comes in contact with a flange 3b provided at the proximal end of the tubular body 3. By cooperating with the distal sloped surface 216b, the flange 3b causes the inner skirt 213 to deflect in the radial and outward direction, thereby freeing the abutment surface 216a from the distal face of the first outer radial stop 211. The second portion 210 is therefore in its unlocked position and free to move proximally with respect to the first portion 209 along the longitudinal axis A of the piston rod 208 until the inner rim 217 of the inner skirt 213 comes in abutment against the second outer radial stop 212 of the first portion 209.

FIGS. 11 to 13B show alternative embodiments of the locking means and deactivating means of a piston rod for an injection device according to the invention.

On FIGS. 11, 11A and 11B is shown an alternative embodiment for the locking means of a piston rod of a device 1 of the invention.

The injection device 1 is provided with a piston rod 308. The piston rod 308 comprises a first portion 309 and a second portion 310. In its proximal region, the first portion 309 is provided with a conical piece 311 made of two half cones 311a and 311b capable of moving with respect to each other (see FIGS. 11A and 11B) in the radial direction due to respective deformations. The cone 311 comprises a central cylindrical bore 312 traversed by a distal rod 313 of the second portion 310. The distal rod 313 is a one-part element provided with at least one circular rim forming a radial surface 313a (see FIGS. 12A and 12B). The two half-cones 311a and 311b are both provided with at least one abutment surface 311c, as shown on FIGS. 12A and 12B which are partial perspective views of the piston rod 308, in which the second half cone 311b has been removed for showing the relative positions of the rod 313 with respect to the half cone 311a in the locked position and in the unlocked position.

On FIG. 11A are shown the cone 311 and the distal rod 313 when the first and second portions (309, 310) of the piston rod 308 are in their locked position. As can be seen on this figure, the respective longitudinal axis (Ba, Bb) of the two half cones 311a and 311b are radially spaced from each other. As shown on FIG. 12A, the radial surface 313a of the piston rod 313 is resting against the rim 311c of half cone 311a. In the same manner, the radial surface 313a of the rod 313 is resting against the rim 311c of half cone 311b (not shown on FIG. 12A). The second portion 310 is therefore fixed with respect to the first portion 309. The second portion 310 is not allowed to move with respect to the first portion 309 because of the respective longitudinal axis (Ba, Bb) of the two half cones 311a and 311b not being confounded.

As explained hereinabove for the previous embodiments, during the injection, the piston rod 308 moves distally: at the end of injection, at least before the piston rod and the piston reach their end-of-injection position, the two half cones 311a and 311b come in contact with the inner wall 3a of the proximal region of the tubular body 3 as shown on FIG. 11 for half cone 311a. The inner wall 3a presses on the two half cones 311a and 311b and makes them slide relative to one another until they reach the relative position shown on FIG. 11B where their respective, longitudinal axis (Ba, Bb) become confounded as shown on FIG. 11B.

Once the two half cones 311a and 311b are aligned so as to reconstitute the cone 311, the first and second portions (309, 310) are in their unlocked position, as shown on FIGS. 11B and 12B. With reference to FIG. 12B, in the unlocked position of the first and second portions (309, 310), the radial surface 313a of the rod 313 is freed from the rim 311c of the cone 311. The second portion 310 is then free to move proximally with respect to the first portion 309 as shown on FIG. 12B.

FIGS. 13A and 13B are partial perspective views of an alternative embodiment of the locking means of the piston rod 308 of FIGS. 12A to 12B, respectively in the locked position and in the unlocked position. In this variant, the rim 311c of the cone 311 of the piston rod of FIGS. 12A to 12B has been replaced by an abutment surface 311d.

On FIG. 14A is shown partially another embodiment of a piston rod 408 of the invention comprising a first portion 409 and a second portion 410. The first portion 409 comprises a rod the proximal region of which is provided with a groove 411 defining a proximal abutment surface 411a and a distal abutment surface 411b. The second portion 410 comprises two clamps 412 (see FIG. 14B) having a semi-annular shape. Each clamp 412 is provided with two ends, one end 412a being fixed to a flexible tongue 413 of the second portion 410, the other end 412b being free and provided with a projection 412d.

On FIGS. 14A and 14B, the first and second portions (409, 410) of the piston rod 408 are in their locked position. For clarity's sake, only one clamp 412 is represented on FIG. 14A. In the locked position of the piston rod 408, the projections 412d of the clamps 412 are engaged in the groove 411 of the first portion 409 and are resting on the abutment surfaces 411a and 411b. The first portion 409 is therefore not allowed to move with respect to the second portion 410 along the longitudinal axis A of the piston rod 408 in both directions, proximal and distal.

When the piston rod 408 and the piston 5 reach their end-of-injection position (not represented), the ends 412a of the clamps 412 come in contact with the internal wall 3a of the tubular body 3. This causes the flexible tongues 413 to deflect radially inwardly and the projections 412d of the clamps 412 disengage from the groove 411 of the first portion 409. The first portion 409 becomes free to move with respect to the second portion 410 along the longitudinal axis of the piston rod 408.

It is evident from the foregoing that the invention provides determinant enhancements over the similar injection devices of the prior art, by making it possible to prevent the proximal return of the piston at the end of injection while the injection needle is still in the injection site and after the protection means have been activated. In particular, because the second portion of the piston rod is fixed to the first portion of the piston rod before use and until the end of the injection step, the user has not the feeling that something may be broken inside the injection device. The user is thus reassured.

The invention makes it possible to benefit from an injection device having automatic protection means while guaranteeing the possibility of injecting the whole dose of product without, for all that, requiring a complex manufacturing method. Specifically, the distance D makes it possible to absorb the dimensional variations.

It goes without saying that the invention is not limited to the embodiment described hereinabove as an example, but that, on the contrary, it embraces all the variant embodiments entering the field of protection defined by the claims appended hereto.

For example, the invention may be applied to other injection devices such as that described in introduction in publication WO 03/068298 A1. In this case, because of the particular design of the piston rod according to the invention, the return energy of the intermediate lugs to their rest position after relaxing the distal pressure exerted on the piston rod is totally absorbed by the proximal movement of the second portion of the piston rod when said second portion is in its unlocked position. Consequently, the first portion and the piston remain immobile and the risk of reabsorption of medicine is thus prevented.

The invention also applies to all the injection devices in which the deformable elastically flexible lugs are replaced for example by:
- inelastic and/or pivoting lugs, acted upon laterally by elastic elements,
- posts travelling in grooves and acted upon laterally by elastic elements,
- an additional rotary element, such as for example a collar placed between the intermediate ring and the sleeve 6, this collar being provided with grooves capable of receiving tabs provided on the sleeve 6 and forming means of retention or of immobilization, this collar being free to pivot.

The invention claimed is:

1. Injection device comprising at least:
   a body designed to receive a product to be injected, said body being provided at its distal end with an injection needle, said body receiving a piston rod and a piston capable of moving in said body between a storage position and an end-of-injection position and of pushing said product through said injection needle,
   a sleeve for covering said injection needle, said sleeve being movable relative to said body between at least an initial position, in which said injection needle is uncovered, and a final position, in which said injection needle is at least partially covered, and
   a spring arranged to move said sleeve between said initial and final positions,
   wherein, said piston rod comprises at least a first portion and a second portion, said first portion and said second portion being axially connected to each other and able to switch between at least a locked position, in which said first portion and said second portion are fixed with respect to each other along the longitudinal axis of said piston rod, and an unlocked position, in which said first portion and said second portion are allowed to move relative to each other at least a predetermined distance along the longitudinal axis of said piston rod, wherein, in said locked position, locking portions of said first portion and said second portion are in interengagement so as to restrict relative movement between said first portion and said second portion along the longitudinal axis of said piston rod, said first portion having a portion with an enlarged cross-section in said locked position, and, wherein, in said unlocked position, said enlarged portion of said first portion being deflected radially inwardly by direct contact with said body to have a smaller diameter cross-section than in said locked position thus causing said locking portions of said first portion and said second portion to be out of interengagement and permit relative movement between said first portion and said second portion along the longitudinal axis of said piston rod.

2. Injection device according to claim 1, wherein said enlarged portion of said first portion coming into direct contact with said body at least before said piston rod reaches the end-of-injection position.

3. Injection device according to claim 1, wherein said locking portions of said first portion and said second portion include at least one flexible element and at least one abutment surface, said flexible element being engaged in said abutment surface when said first portion and said second portion are in said locked position.

4. Injection device according to claim 1, wherein, in said unlocked position, said enlarged portion of said first portion comes into direct contact with an inner wall of said body.

5. Injection device according to claim 1, wherein, in said unlocked position, said enlarged portion of said first portion comes into direct contact with a flange provided at a proximal end of said body.

6. Injection device according to claim 1, wherein said locking portions of said first portion and said second portion include at least a first element having a first longitudinal axis and at least a second element having a second longitudinal axis, said first and second longitudinal axes being radially spaced from each other when said first portion and said second portion of said piston rod in said locked position so as to provide said enlarged portion with said enlarged cross-section, at least one of said first and second elements being movable so as to cause said first and second longitudinal axes to become confounded under the action of being deflected radially inwardly by direct contact with said body, thereby causing said first portion and said second portion of said piston rod to switch to said unlocked position.

7. Injection device according to claim 6, wherein an inner wall of said body corning in direct contact with at least one of said first and second elements and thereby forcing said first and second elements to become axially aligned with each other, at least before said piston rod and said piston reach their end-of-injection position.

8. Injection device according to claim 1, said said spring is arranged to move said second portion in the proximal direction with respect to said first portion when said first portion and said second portion are in said unlocked position.

9. Injection device according to claim 1, wherein said first portion is provided with a first stop and said second portion is provided with a second stop, said first and second stops being capable of cooperating with each other so as to prevent further proximal movement of said second portion with respect to said first portion, after said second portion has moved proximally with respect to said first portion said predetermined distance, when said first portion and said second portion are in said unlocked position.

10. Injection device according to claim 1, characterized in that said predetermined distance is less than 10 mm.

11. Injection device according to claim 10, characterized in that the said predetermined distance is less than or equal to 5 mm.

12. Injection device according to claim 11, characterized in that the said predetermined distance is less than or equal to 3 mm.

* * * * *

UNITED STATES PATENT AND TRADEMARK OFFICE
CERTIFICATE OF CORRECTION

PATENT NO. : 8,628,499 B2  Page 1 of 1
APPLICATION NO. : 12/744022
DATED : January 14, 2014
INVENTOR(S) : Grégory Peruzzo It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this
Twenty-second Day of September, 2015

Michelle K. Lee
*Director of the United States Patent and Trademark Office*